United States Patent [19]

Uchiyama et al.

[11] Patent Number: 5,059,290
[45] Date of Patent: Oct. 22, 1991

[54] ELECTROANALYTICAL METHOD

[75] Inventors: Shunichi Uchiyama, Fukaya; Shuichi Suzuki, Tokyo, both of Japan

[73] Assignee: Mitsui Engineering & Shipbuilding Co., Ltd., Tokyo, Japan

[21] Appl. No.: 301,792

[22] Filed: Jan. 25, 1989

[30] Foreign Application Priority Data

Jan. 29, 1988 [JP] Japan .................................. 63-18696

[51] Int. Cl.$^5$ ............................................. G01N 27/26
[52] U.S. Cl. .............................. 204/153.1; 204/153.12; 204/400; 204/403; 204/409
[58] Field of Search ................ 204/1 T, 400, 409, 435, 204/431, 432, 403, 153.1, 153.12

[56] References Cited

U.S. PATENT DOCUMENTS

| | | | |
|---|---|---|---|
| 3,291,705 | 12/1966 | Hersch | 204/153.16 |
| 3,296,113 | 1/1967 | Hansen | 204/409 |
| 3,315,271 | 4/1967 | Hersch et al. | 204/153.13 |
| 3,839,162 | 10/1974 | Ammer | 204/409 |
| 3,846,270 | 11/1974 | Muto et al. | 204/409 |
| 3,926,764 | 12/1975 | Ruzicka et al. | 204/435 |
| 3,928,162 | 12/1975 | Takata | 204/409 |
| 4,214,968 | 7/1980 | Battaglia et al. | 204/418 |
| 4,533,456 | 8/1985 | Kratochvil et al. | 204/415 |
| 4,576,706 | 3/1986 | Takata et al. | 204/409 |

FOREIGN PATENT DOCUMENTS

87/03624  6/1987  PCT Int'l Appl. .

Primary Examiner—T. Tung
Attorney, Agent, or Firm—Fay, Sharpe, Beall, Fagan, Minnich & McKee

[57] ABSTRACT

An electroanalytical method which can detect and determine a substance in a short time, with stability and simply is provided, which method comprises
  providing an electrolytic cell provided with a working electrode chamber and a counter electrode chamber adjacent thereto by the medium of a separator electrolyzing a sample to be determined, by feeding it to a working electrode contained in the working electrode chamber and consisting of an electroconductive porous body impregnated with an electrolyte in a non-flowing state; and measuring at least one of the electric voltage, electric current and electrical quantity in the working electrode, to determine the substance in the sample.

8 Claims, 2 Drawing Sheets

ELECTROANALYTICAL METHOD

BACKGROUND OF THE INVENTION

1. Field of the Invention

This invention relates to an electroanalytical method of subjecting a substance to be determined to a determination based on change in the electrolytic voltage, electrolytic current or electrolytic coulomb number in the process of electrolysis of the substance to the determined.

2. Field of the Invention

An electrochemical analytical method has recently been broadened in its fields of use. The method is used in connection with the so-called biosensor, liquid-chromatographic detector, and in other areas.

Conventional methods for detecting specimens according to the electroanalytical method include a method of immersing a detecting electrode such as an ion selective electrode, biological electrode, etc. in a sample solution, a method of forcibly flowing a sample solution inside a working electrode as in the case of chromatographical detector or flow injection detector, and a method of directly feeding a sample into an electrolyte as in the case of Karl Fischer method for moisture determination.

The above-mentioned prior art, however, has raised various problems. For instance, since a substantial amount of time is required for washing the electrode part, an analytical time as a whole is prolonged. In the case of insufficient washing, analytical accuracy is notably reduced. Also, the background level is so high that the art is unsuitable to microanalysis, and there is a limitation in the reduction of the detector volume. Thus the determination time itself is too long. Accordingly the art has not been satisfactory. Thus, for example, even in the case of iodometry broadly employed according to manual analysis, only potentiometers and galvanic cells have been proposed as instruments for use in automatic analysis.

SUMMARY OF THE INVENTION

The object of the present invention is to provide an electroanalytical method which overcomes the above-mentioned problems of the prior art and offers a high accuracy and a superior operability.

The present inventors have noted that during the entire period of the analytical time required for the electroanalysis, the time required for washing the detector is considerably long. Also when the measurement is carried out while the electrolyte is flowed as it is, the background or noise level due to the uncontrolled flow rate becomes so relatively high that the detection limit value increases. The inventors have further found that when an electrode consisting of an electroconductive porous body is impregnated with an electrolyte to such an extent that it does not flow out of the body and a sample is directly fed to the electrode to carry out electrolysis, then it is possible to effect the analysis rapidly and with a high accuracy.

The present invention resides in:

an electroanalytical method which comprises providing an electrolytic cell containing a working electrode chamber and a counter electrode chamber which are divided by an ion-exchange membrane;

electrolyzing a sample to be determined, by directly feeding it to a working electrode contained in said working electrode chamber and consisting of an electroconductive porous body impregnated with an electrolyte in a non-flowing state;

and measuring at least one of the electrolytic voltage, electrolytic current and electrolytic coulomb number in said detecting electrode, to determine said substance to be determined in said sample.

Figure 1:
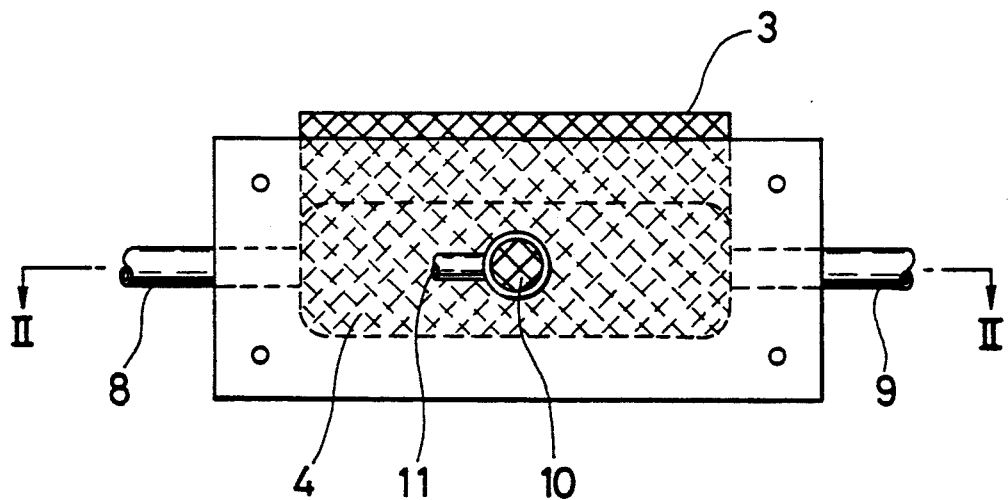
FIG. 1 shows a view illustrating an embodiment of an electrolytic cell used in the present invention.

1 —— ion exchange membrane, 2 —— working electrode,
3 —— current-collecting metal gauze,
5 —— counter electrode, 6 —— current-collecting plate, 10 —— sample-feeding tube,
11 —— inert gas-flowing-in port

DETAILED DESCRIPTION OF PREFERRED EMBODIMENTS

When a substance to be determined is electrolyzed in an electrolytic cell, the resulting electrical change in quantity i.e. change in the electric voltage, electric current or electrical quantity is related to the quantity of the substance electrolyzed; hence it is possible to determine the substance to be determined, by measuring the electrolytic coulomb number changed at the time of the electrolysis.

In the present invention, a mere porous membrane may be used, but in order to reduce the background level, it is preferred to use a highly electroconductive ion-exchange membrane.

In the present invention, as a material for the working electrode, it is preferred to use an aggregate of carbonaceous or graphitic carbon fibers such as a carbon felt or a porous carbon, on the surface of which an element heavier than carbon is present in 1.5% or more in terms of the proportion of numbers of the surface elements as measured according to ESCA (Electron Spectroscopy for Chemical Analysis of photoelectric spectrophotometry). Such an electrode consisting of carbon fibers is disclosed in Japanese patent application No. Sho 63-283985. The element made coexistent with carbon is introduced onto the surface of the detecting electrode in the form of a carbide or some other compound of silicon or other elements including those of group V, group VI and group VII of the Periodic Table, whereby the dispersibility of the sample solution is improved and at the same time, in the electrolytic reaction, an electron transfer reaction between the working electrode and the substance to be electrolyzed is rapidly carried out.

It is important that materials for the working electrode and materials for current-collecting gauze or wire are chemically stable. For example, nickel gauze, sintered porous nickel, etc. may be used in an alkaline electrolyte, and materials of noble metals such as platinum may be used in various kinds of electrolytes. These materials, however, are often inferior in the dispersibility and seizability of the sample solution to the above carbon fibers or porous carbon.

In the present invention, the shape of the working electrode is preferred to be a shape larger than a disk having a thickness of 1.5 mm or more and a diameter of 10 mm, whereby a sufficient volume for diffusing the sample solution is secured so that the sample solution is able to diffuse rapidly. If the thickness is less than 1.5 mm or the diameter is less than 10 mm, the electrode volume is insufficient so that it is impossible to diffuse the dropped sample rapidly and uniformly and hence the time required for the analysis is prolonged and the response curve is disturbed to make the analysis troublesome.

In the working electrode, a lead wire is usually taken out of a current-collecting metal gauze, and in the case of analysis wherein only a relatively low current flows, it is possible to extend the detecting electrode as it is, to the outer part of the cell to collect current, or it is also possible to make arranged carbon fibers a current-collecting cloth or a lead filament.

As the electrolyte used in the present invention, various pH buffer solutions are enumerated, and materials obtained by dissolving or dispersing therein, e.g. iodide compounds represented by KI, metal complexes of iron, cobalt, molybdenum, etc., complex ligands of halogen ions, aminocarboxylic acids, enzymes, etc. which function as a redox mediator and/or an auxiliary substance may also be used.

In the present invention, electrolytic reaction is carried out in a state where the working electrode is impregnated with the electrolyte, i.e. in a state where the electrolyte is standing still. Since the electrolyte is not passed therethrough, the electrolytic reaction is completed to the last, and since the background becomes extremely small, the analytical accuracy is improved.

As a method of feeding the sample solution onto the working electrode, methods of using a quantitative pipette, microsyringe, etc. may be illustrated. In the case where the sample is non-aqueous or oily, when the sample is injected into the detecting electrode by means of a microsyringe, it is possible to improve the analytical accuracy and also shorten the analytical period of time.

In the present invention, if the substance to be determined in the sample solution causes no direct electron transfer reaction with the detecting electrode, it is preferred to employ a redox mediator and/or an auxiliary reagent which can convert the substance to be determined into an active substance to the electrode reaction such as enzymes, coexistent in the electrolyte by dispersing or fixing it. Examples of the redox mediators are halogen ion/halogen system, hydroquinones/quinones system, (e.g. naphthoquinonesulfonic acid), polyvalent metal ions, etc. Enzymes used as auxiliary substances include those which react with the substance to be determined to generate hydrogen peroxide as in the case of glucose, and besides those which form an active substance to the working electrode by the medium of redox mediators.

In the present invention, if necessary, it is preferred to introduce an inert gas such as nitrogen through an inert gas-flowing-in port provided in the sample-feeding tube to thereby prevent interference caused by oxygen in the atmosphere. Renewal of the electrolyte may be carried out through the electrolyte-flowing-in tube and the electrolyte-flowing-out tube each connected to the working electrode chamber.

The present invention will be described in more detail by way of Examples.

Figure 2:
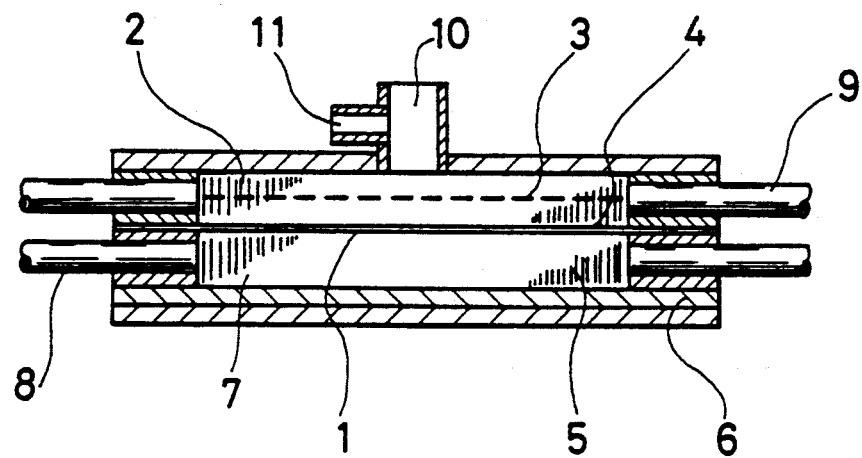
FIG. 2 shows a cross-sectional view of FIG. 1 in the direction along II—II line indicated by arrow marks.

As described above, FIG. 1 shows a view illustrating an embodiment of a detector (electrolytic cell) used in the present invention and FIG. 2 shows a cross-sectional view of FIG. 1 in the direction along a II—II line indicated by arrow marks. The electrolytic cell is composed of a separator 1 and a working electrode chamber 4 and an counter electrode chamber 7 respectively provided on both sides of separator 1, placing the separator between these chambers; a working electrode 2 consisting of an electroconductive porous body is filled in a working electrode chamber 4 and also a current-collecting metal wire gauze 3 is contained therein; and a sample-feeding tube 10 provided with an inert gas-flowing-in port 11 is connected to the chamber. On the other hand, in a counter electrode chamber 7 are contained a counter electrode 5 consisting of an electroconductive porous body and a current-collecting plate 6 consisting of a carbon plate. In addition, numerals 8 and 9 show an electrolyte-flowing-in tube and an electrolyte-flowing-out tube each connected to the working electrode chamber and the counter electrode chamber.

In such a construction, a sample containing a substance to be determined is fed onto the detecting electrode 2 impregnated with an electrolyte through the sample-feeding tube 10 by means of a quantitative pipette or the like; electrolyzed; and determined by measuring at least one of the electrolytic voltage, electrolytic current and electrolytic coulomb number in the working electrode 2.

Next, a concrete embodiment of the present invention using the electrolytic cell shown in FIG. 1 will be described.

The present invention is applied to various coulometric, amperometric and voltammetric analyses for substances in water, food, blood, chemical products, etc.

EXAMPLE 1

An electrolytic cell as a detector was formed using a polystyrenesulfonic acid membrane as the separator 1, a material obtained by feeding oxygen onto the surface of a polyacrylonitrile fiber based carbon felt obtained by baking at 1,400° C. and having a proportion of numbers of the surface elements, O/C of 1.7% measured according to ESCA (Electron Spectroscopy for Chemical Analysis) as the working electrode 2 and the counter electrode 5 and a platinum gauze as the current-collecting metal gauze 3, respectively O/C is defined as a ratio of the number of bonded oxygen atoms calculated from $O_{1s}$ spectra according to ESCA surface analysis to the number of carbon atoms calculated from $O_{1s}$ spectra according to ESCA surface analysis.

Using as a working electrolyte, an aqueous solution of acetic acid-sodium acetate containing KI of pH 3.5 and on the other hand, using as a counter electrode solution, an aqueous solution of acetic acid-sodium acetate containing iodine and iodine ion and at a potential of the working electrode of $-0.5V$ vs. the counter electrode, residual chlorine in tap water was determined (controlled potential coulometry).

Addition of the tap water as sample was carried out with a 100 μl quantitative pipette (Eppendorf pipet) and an inert gas was not introduced.

The quantitative values sought in this Example accorded well with those sought according to orthotolidine method and iodine titration method. Further, as to dispersion, that according to the present invention was minimum as shown in Table 1.

TABLE 1

| | Residual chlorine in tap water (ppm) | | |
|---|---|---|---|
| Number time of analysis | Method of present invention | Orthotolidine method | Iodine titration method |
| 1 | 0.42 | 0.4 | 0.48 |
| 2 | 0.43 | 0.3 | 0.40 |
| 3 | 0.37 | 0.5 | 0.35 |
| 4 | 0.39 | 0.4 | 0.55 |
| 5 | 0.41 | 0.3 | 0.50 |

In addition, a once analytical time according to the method of the present invention was about 1/30–1/40 that of orthotolidine method.

Further, the average value of five times analyses of residual chlorine in the same tap water with 10 µl quantitative pipette was 0.40 ppm and the range was 0.081 ppm.

EXAMPLE 2

Using the same detector and electrolytes as those in Example 1, the respective $CCl_4$ solutions of a glycerol oleate just after opening of a sealed vessel thereof and those after opening of the vessel and exposed to direct sunlight for 3 hours were fed onto the detector 2 by means of a quantitative pipette to detect lipid hydroperoxide peroxides in the glycerol oleate.

The peak value of the reduction current in the working electrode 2 obtained by adding the glycerol oleate just after the opening was about 15 µA and almost unchanged from that of the background level, whereas the peak value of the glycerol oleate after allowed to stand for 3 hours amounted to 250 µA. This tendency accorded with the results of the measurement method of peroxides in food analysis.

COMPARATIVE EXAMPLE 1

Example 2 was repeated except that a polyolefin microporous membrane was used as the separator and the O/C value on the surface of the detecting electrode according to ESCA was made about 1%, to detect the lipid peroxide.

Since the working was changed, the background level rose to reduce the sensibility, it was impossible to detect the lipid peroxide in the oils and fats just after the opening of the sealed vessel. Further, since the O/C value of the detecting electrode was reduced, the dispersibility, etc. of the sample lowered to require 1.5 times the determination time.

EXAMPLE 3

Oxygen dissolved in water was detected using the detector of Example 1; using a phosphoric acid-sodium phosphate aqueous solution (pH: 5.5) of 0.2M-ethylenediaminetetracarbonatoiron (II) as the working electrolyte and a phosphoric acid-sodium phosphate aqueous solution of $KI-I_2$ as the counter electrode solution, making the potential of the working electrode −0.65V vs. the counter electrode; and further introducing nitrogen gas through an inert gas-introducing port. The sample volumes at four stages were 10 µl, 25 µl, 50 µl and 100 µl, respectively, and the peak current values at the respective stages were measured.

Figure 3:
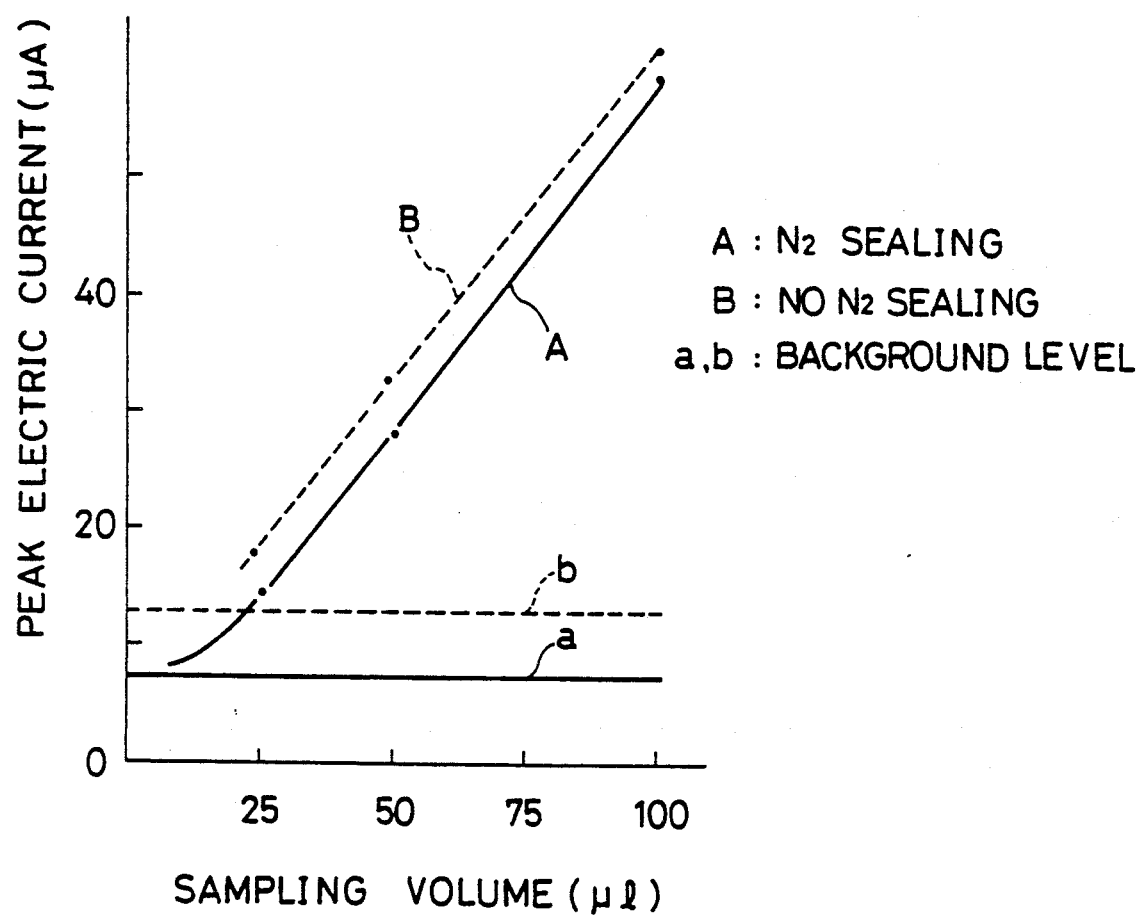
FIG. 3 shows a chart illustrating the relationship between the quantity of a sample fed and the peak electric current value in Example 3.

The measurement results are shown in FIG. 3. Nitrogen gas-passing water as a blank exhibited no peak current. Further, when the inside of the working electrode chamber was not sealed with nitrogen gas, the background level rose; thus in the case where the sample volume was 10 µl, dissolved oxygen could not be detected.

EXAMPLE 4

An electrolytic cell was formed using a sulfonic acid cationic ion-exchange membrane using a polyolefin as its substrate; nitrogen as a sealing inert gas; a carbon felt electrode having a proportion of numbers of the surface electments O/C of 5% and that having a proportion of numbers of the surface elements Cl/C of 3%, as the working electrode 2 and as the counter electrode 5, respectively; and a graphite plate as the current-collecting plate 6 of the counter electrode Using an aqueous solution of $1M-NaH_2PO_4$ as the electrolyte of the working electrode 2 and on the other hand, an aqueous solution of 0.2M-KI and $1M-NaH_2PO_4$, as the counter electrode solution, ethylenediaminetetracarbonatoiron (III) (Fe(III)EDTA) in an aqueous solution of 1mM-Fe(III)EDTA was determined.

The determination results are shown in Table 2.

TABLE 2

| | Sample volume | |
|---|---|---|
| Item | 10 (µl) | 100 (µl) |
| Range of five times measurements (value divided by average value) | 14.2 (%) | 0.06 (%) |
| Average value divided by theoretical value | 93.0 (%) | 104.4 (%) |

(Note) Theoretical value: calculated value according to weight method, making the proportion of Fe(III)EDTA reagent 100%.

The determination results have a high repetition accuracy and also a high reliability.

According to this Example, restrictions to hydrolytic engineering such as the mixing part of the substance to be determined with the electrolyte, flow quantity-controlling mechanism, etc. are unnecessary to make it possible to simplify the total flow lines and also to effect a quantitative analysis having a high reliability.

COMPARATIVE EXAMPLE 2

A quantitative analysis was carried out under the same conditions as in Example 1 except that sealing nitrogen gas feed was stopped. As a result, the analytical value was abnormally large, there was no reproducibility and determination was impossible.

COMPARATIVE EXAMPLE 3

A quantitative analysis was carried out under the same conditions as in Example 1 except that electrolysis was carried out while passing the electrolyte as it was. As a result, the background current rose up to a value close to two figures and was unstabilized so that the analytical accuracy lowered notably. This is considered due to the fact that cross mixing of the electrolytes through the separator increased.

EXAMPLE 5

The determination in Example 4 was carried out according to a constant-current method of seeking the endpoint from change in the potential. As a result, the determination could be carried out with an accuracy almost same with that in the case of controlled potential coulometry.

EXAMPLE 6

An electrolytic cell was constructed using a polystyrenesulfonic acid cation-exchange membrane as the separator 1, a carbonaceous carbon felt having the same properties as those of the felt used in Example 4 as the working electrode 2, a stainless mesh as the current-collecting metal gauze 3 for the working electrode 2 and a graphite plate as the current-collecting plate 6 for the counter electrode 5, respectively, and as a substance for exchanging the substance to be determined with the electroactive substance, immobilized enzyme (glucose oxidase) glass beads were dispersed in the working electrode 2. Further, as the electrolyte for the working electrode, 2, an electrolyte having KI added to a buffer solution having a pH of 5.8 was used and on the other hand, as the solution for the counter electrode, as 0.5M-KI aqueous solution of a pH of 4 was used, and these solutions were sometimes exchanged with a fresh solution, respectively.

Glucose was detected using the above-mentioned electrolytic cell, making the potential of the working electrode −0.65V vs. the counter electrode and pouring an aqueous solution of 0.1% by weight glucose (25 μl) as a sample in the working electrode.

It is difficult to directly electrolyze glucose, but since the glucose is converted into gluconolactone and hydrogen peroxide due to the function of the glucose oxidase as a catalyst, it is possible to detect and determine the hydrogen peroxide through the $I_2$ determination.

According to this Example, even a substance difficult to be directly determined by the electrode reaction can be exchanged with an electroactive substance due to the function of enzyme, etc. as an auxiliary; hence the electrode reaction can proceed easily to make the detection and determination possible.

In this Example, the background current was about 10 μA, but the observed value was smaller by about 25% that the theoretical electrical quantity. This was due to glucose isomer; thus by adding mutarotase (Aldose-1-epimerase) capable of converting α-D-glucose into β-D-glucose to function, determination just as in the theoretical electrical quantity became possible.

According to the method of current observation, by reading a plateau (steady current) value attained within a few minutes in ordinary circumstances after feed of a sample to be tested (serum) to the working electrode containing the substrate of the enzymatic reaction and using for example the following equation based on the above value, it is possible to obtain an enzyme activity $\rho$ (unit: unit/ml, etc.);

$$\rho(\mu mol/min) = 3.1 \times 10^{-4} \times Ist$$

(Ist: steady current value).

According to this method, the measurement time is shortened and also operation is simplified as compared with other conventional spectrophotometric enzymic method.

EXAMPLE 7

The concentration of L-ascorbic acid of reduced type in various foods were measured according to controlled potential coulometry using ferricyan ion as oxidation mediator. The construction of the detector was made as follows:

working electrode: a carbon felt of 38 mmφ in diameter and 3 mm thick which was made from polyacrylonitrile fibers was impregnated with a buffer solution of phosphoric acid-sodium phosphate (pH 4) containing saturated potassium ferricyanate at room temperature, counter electrode: same as the detector, separator: cation-exchange membrane (Naphion 117 trademark of Du Pont Co.)

Juice sample was used as it was or diluted with distilled water and dropwise fed onto the working electrode by means of a 10 μl quantitative pipette. As to citrus sample, the squeezed juice was filtered through a 0.45 μm filter and then similarly fed onto the working electrode by means of a 10 μl quantitative pipette. Analytical results according to the present method and comparative methods are shown in Table 3.

TABLE 3

| Sample | Present method | Indophenol method | Liquid chromatography (HPLC) |
| --- | --- | --- | --- |
| Lemon soft drink | 182 mgl$^{-1}$ | 191 mgl$^{-1}$ | |
| Grape fruit juice | 257 mgl$^{-1}$ | 249 mgl$^{-1}$ | |
| Orange | 2.0 | | 2.2 |
| Tomato | 1.9 | | 1.8 |

EXAMPLE 8

Measurement of cholesterol in serums were carried out using a detector having the same shape as in Example 7. Solutions with which two electrodes were impregnated and substances dispersed therein were as follows:

working electrode: Phosphoric acid-sodium phosphate buffer solution (pH 6.8), about 0.2M potassium ferrocyanate, cholesterol oxidase (5.5 mg ml$^{-1}$) and peroxidase (13.8 ml$^{-1}$ counter electrode: acetic acid-sodium acetate buffer solution (pH 4), saturated KI An electrical quantity based on free cholesterol was sought from a current-time curve obtained by the above measurement. Further, cholesterol esterase was dispersed on the side of the working electrode and the same measurement was carried out to seek a current peak based on the total cholesterol.

The respective serum samples of human being, horse and bovin were measured using commercially available abbreviated analysis kits (free cholesterol "Free-Cholesterol C-test, Wako" and total cholesterol "Cholesterol C-test, Wako"). The deviations of the measurements were 10% or less relative to the results of the present method. As to free cholesterol, it is possible to easily prepare a standard solution, and with standard solutions of $1 \times 10^{-3}$M and $1 \times 10^{-4}$M, the differences between the measured values in the case of the present method and the calculated values according to weight method were 3% or less.

EXAMPLE 9

A carbon felt working electrode of 38 mmφ in diameter an 3 mm thick was impregnated with ascorbic acid oxidase and KI, and a current under which iodine formed by air oxidation was electrolytically reduced was measured followed by feeding a sample containing vitamin C (L-ascorbic acid of reduced type) to the working electrode and measuting lowering of the reduction current caused by the oxygen consumption reaction to thereby determine vitamin C.

In this method, particularly reproducibility was improved by immobilizing the enzyme onto the working electrode. The enzyme was immobilized according to two method. According to one of them, a polyacrylamide derivative to be dispersed in the working electrode was diazotized with nitrous acid and ascorbic acid oxidase was immobilized by subjecting the resulting material to coupling reaction with the derivative. According to the other method, the carbon felt electrode was nitrated, followed by aminating the resulting material through reduction and carrying out diazo-coupling as described above to effect immobilizing.

The results similarly exhibited very good response properties and reproducibility.

As described above, according to the present invention, it is possible to detect and determine a substance to be determined in a short time and with stability and also to simplify the flow line of the whole of the equipment. Further, it is possible to very easily carry out the determination of enzyme activity for clinical inspections.

What we claim is:

1. An electroanalytic method comprising the steps of:
    providing an electrolytic cell comprising a working electrode chamber and a counter electrode chamber separated by an ion-exchange membrane, the working electrode chamber including a working electrode comprising a circular electroconductive porous body having a non-flowing electrolyte impregnated in the pores of said electroconductive porous body;
    feeding a liquid sample directly to the working electrode whereby the liquid sample diffuses into the porous body of the working electrode for determining an identity of a substance within said liquid sample; and
    determining the identity of a substance within said liquid sample by measuring at least one of electrical quantity, electrical voltage or electrical current within said working electrode whereby the electrolyte is unmoving.

2. An electroanalytic method, according to claim 1, wherein said working electrode is of a circular disk configuration having a diameter at least about 10 mm and a thickness of at least about 1.5 mm.

3. An electroanalytic method, according to claim 1, wherein said working electrode is comprised of an aggregate of carbonaceous or graphitic carbon fibers.

4. An electroanalytic method, according to claim 1, wherein said working electrode is comprised of porous carbon.

5. An electroanalytic method, according to claim 1, wherein said electrolyte includes a redox mediator or an auxiliary reagent for activating the substance to be determined such that the electrical quantity can be measured.

6. An electroanalytic method, according to claim 5, wherein said auxiliary reagent is an enzyme.

7. An electroanalytic method comprising the steps of:
    providing an electrolytic cell comprising a working electrode chamber and a counter electrode chamber separated by an ion-exchange membrane, the working electrode chamber including a working electrode comprising a circular electroconductive porous body having a nonflowing electrolyte impregnated in the pores of said electroconductive porous body, and a sample-feeding tube provided at the upper portion thereof;
    feeding a liquid sample directly to the working electrode through said sample-feeding tube whereby the liquid sample diffuses into the porous body of the working electrode for determining an identity of a substance within said liquid sample; and
    determining the identity of a substance within said liquid sample by measuring at least one of electrical quantity, electrical voltage or electrical current within said working electrode whereby the electrolyte is unmoving.

8. An electroanalytic method, according to claim 7, wherein said working electrode is of a circular disk configuration having a diameter at least about 10 mm and a thickness of at least about 1.5 mm.

* * * * *